United States Patent [19]

Rao et al.

[11] 4,144,138
[45] Mar. 13, 1979

[54] RECOVERY OF ETHERS

[75] Inventors: Babu Y. Rao, Fishkill; Sheldon Herbstman, Spring Valley, both of N.Y.; Michael D. Riordan, Houston, Tex.

[73] Assignee: Texaco Inc., New York, N.Y.

[21] Appl. No.: 870,406

[22] Filed: Jan. 18, 1978

[51] Int. Cl.² .................. C07C 41/12; B01D 3/36
[52] U.S. Cl. .......................... 203/46; 203/71; 203/81; 203/DIG. 19; 568/699
[58] Field of Search ............ 203/63, 66, 46, 81, 203/74, 18, 14, 99, DIG. 19; 260/614 A, 616; 568/913

[56] References Cited
U.S. PATENT DOCUMENTS

| 2,581,789 | 1/1952 | Forman | 203/82 |
| 3,940,450 | 2/1976 | Lee | 203/70 |
| 3,979,461 | 9/1976 | Ancillotti et al. | 260/614 A |
| 4,071,567 | 1/1978 | Ancillotti et al. | 260/614 A |

Primary Examiner—Wilbur L. Bascomb, Jr.
Attorney, Agent, or Firm—Thomas H. Whaley; Carl G. Ries; Carl G. Seutter

[57] ABSTRACT

Methyl tertiary butyl ether may be recovered from etherification reaction effluent by azeotropic distillation to recover methanol-ether azeotrope overhead which is water-washed to give pure ether raffinate plus ether-methanol bottoms, the latter being azeotropically distilled to yield ether-methanol overhead which is recycled to water-washing.

9 Claims, 1 Drawing Figure

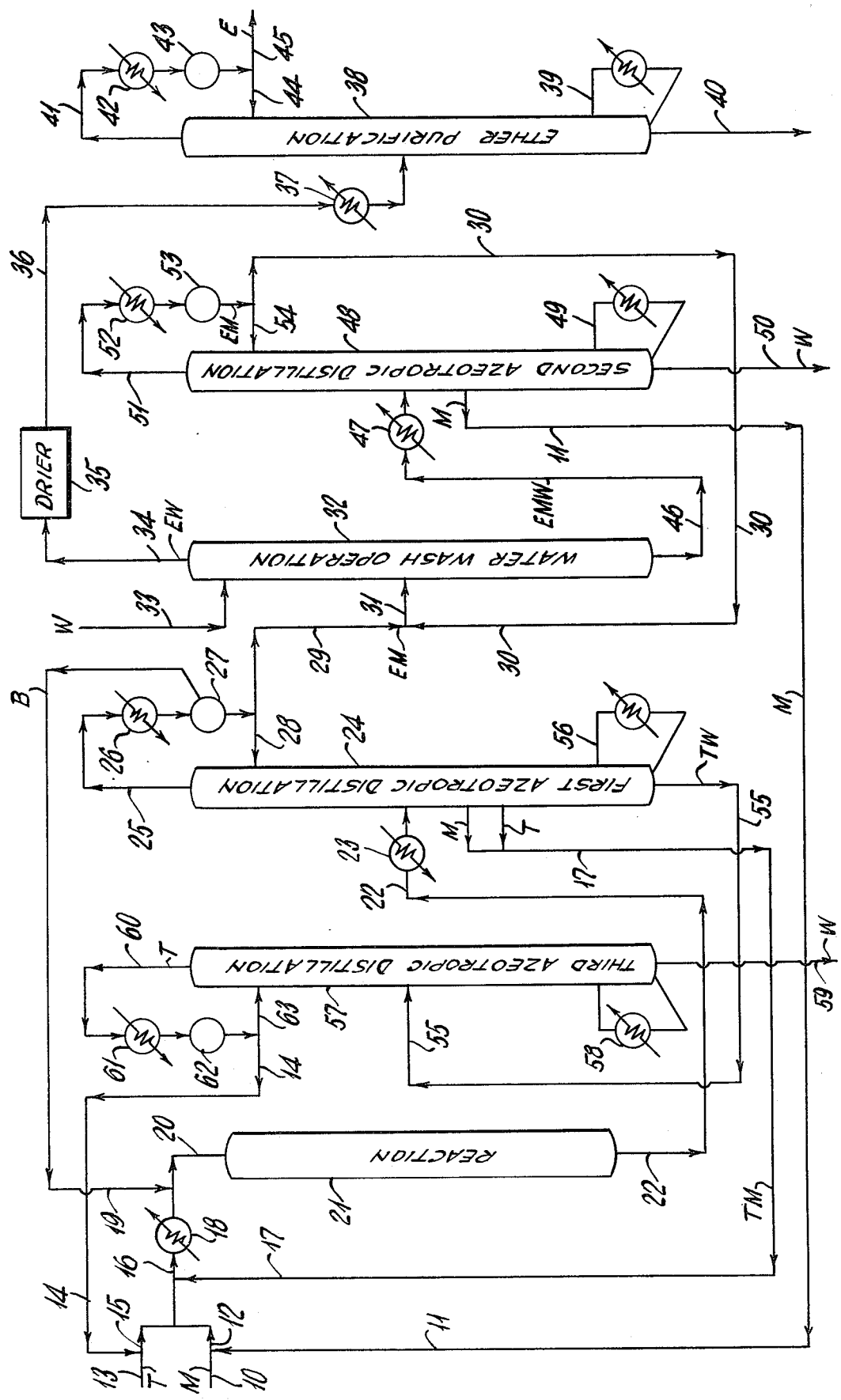

RECOVERY OF ETHERS

FIELD OF THE INVENTION

This invention relates to the preparation of ethers. More particularly it relates to the preparation of unsymmetrical ethers in high yield and purity.

BACKGROUND OF THE INVENTION

As is well known to those skilled in the art, ethers, including unsymmetrical ethers, may be prepared by reacting an alcohol with another alcohol to form the desired product. The reaction mixture, containing catalyst and/or condensing agent, may be separated and further treated to permit attainment of desired product. Such further treatment commonly includes one or more distillation operations.

It is an object of this invention to provide a process for preparing ethers. Other objects will be apparent to those skilled in art from the following description.

SUMMARY OF THE INVENTION

In accordance with certain of its aspects, the novel method of this invention for recovering methyl t-butyl ether from a reaction effluent containing methyl t-butyl ether, methanol, t-butanol, and water may comprise;

(a) distilling said reaction effluent in a first azeotropic distillation operation thereby forming an overhead containing an azeotrope of methanol and methyl t-butyl ether;

(b) water-washing said azeotrope in a water-washing operation thereby forming (i) a raffinate containing methyl t-butyl ether and (ii) an extract containing water, methanol, and methyl t-butyl ether;

(c) recovering said raffinate containing methyl t-butyl ether;

(d) distilling said extract in a second azeotropic distillation operation thereby forming (i) an overhead stream containing methanol and methyl t-butyl ether and (ii) a bottoms stream containing water; and (e) passing said overhead stream from said second azeotropic distillation operation to said water-washing operation.

DESCRIPTION OF THE INVENTION

Preparation of the product ether of this invention may be carried out typically by reacting methanol with t-butanol. Although the reactants may be impure, it is preferred that they be of reasonable purity.

Reaction may be carried out utilizing the following reaction conditions:

TABLE

| Conditions | Broad Range | Preferred Range | Preferred Value |
|---|---|---|---|
| Temperature, °C. | 40–200 | 70–150 | 120 |
| Pressure, psig | 50–750 | 50–500 | 100 |
| Methanol (parts) | 150–1500 | 150–750 | 528 |
| t-butanol (parts) | 150–1500 | 150–700 | 500 |

It is a particular feature of the process of this invention that the mole ratio of the methanol to the t-butanol may be at least about 2.0. It will be found that the advantages inherent in the process may be attained to a greater degree if this ratio is greater than 2 and preferably 2.2–5 say 2.5. Presence of the excess of methanol facilitates purification of the desired unsymmetrical ethers.

Etherification may be preferably carried out in the presence of a solid resin etherification catalyst. These catalysts may be relatively high molecular weight carbonaceous materials containing at least one $-SO_3H$ group as the functional group. Typical of these catalysts are the sulfonated coals ("Zeo-Karb H", "Nalcite X" and "Nalcite AX") produced by the treatment of bituminous coals with sulfuric acid. These materials are usually available in a neutralized form and in this case must be activated to the hydrogen form by treatment with a strong mineral acid such as hydrochloric acid, followed by water-washing to remove sodium and chloride ions prior to use.

The sulfonated resin type catalysts are preferred for use in the present invention. These catalysts include the reaction products of phenol-formaldehyde resins and sulfuric acid ("Amberlite IR-1", "Amberlite IR-100", and "Nalcite MX"). Also useful are the sulfonated resinous polymers of coumarone-indene with furfural; sulfonated polymers of coumarone-indene with cyclopentadiene and furfural; and sulfonated polymers of cyclopentadiene with furfural.

The most preferred cationic exchange resins are strongly acidic exchange resins consisting essentially of sulfonated polystyrene resin: for instance, a divinylbenzene cross-linked polystyrene matrix having 0.5–20% and preferably 4–16% of copolymerized divinylbenzene therein, bearing ionizable or functional nuclear sulfonic acid groups. These resins are manufactured and sold commercially under various trade names such as "Dowex 50", "Nalcite HCR" and "Amberlyst 15". As commercially obtained they have a solvent content of about 50% and can be used as is or the solvent can be removed first. The resin particle size may typically be 10 to 50 mesh (United States Sieve Series).

The reaction may be carried out in either a stirred slurry reactor or in a fixed bed continuous flow reactor. The catalyst concentration should be sufficient to provide the desired catalytic effect. Generally in a stirred reactor, catalyst concentration should be 0.1%–10% (dry basis) by weight of the reaction contents, 0.2 to 5% being the preferred range.

There may thus be added to the reaction operation in a preferred embodiment, 528 parts of methanol and 500 parts of t-butanol. During reaction, the desired product methyl t-butyl ether is formed by reaction of methanol and t-butanol. Etherification is preferably carried out at 40° C–200° C, preferably 70° C–150° C, say 120° C; and the pressure may be 50–750 psig, preferably 50–500 psig, say 100 psig.

The typical crude product stream may contain 121–563 parts, say 402 parts of methanol, 27.3–127 parts, say 91 parts of t-butanol, 116–538 parts, say 385 parts of methyl tertiary butyl ether, 17.7–82 parts, say 59 parts of isobutene, and 27–129 parts, say 91 parts of water.

The crude product stream so obtained is cooled to 65° C–120° C, say 71° and passed to a first azeotropic distillation operation.

First azeotropic distillation overhead is recovered in the amount of 2078–9662 parts, say 6912 parts at 65° C–117° C say 83° C and 0–30 psig, say 15 psig; and 1922–8938 parts, say 6394 parts are returned as pumped reflux. Net product includes 2–9 parts, say 6 parts of methanol and 136–633 parts, say 453 parts of azeotrope containing 13–17 w%, say 15 w% methanol, 83–87 w%, say 85 w% of methyl tertiary butyl ether. 18–82 parts, say 59 parts of non-condensibles (isobutene) are withdrawn; the non-condensibles are recovered and may be recycled to etherification.

Alternatively, the crude product stream may be passed to a separation operation wherein 18–82 parts, say 10 parts of isobutene are flashed off. This isobutene, depending on its purity, may be recycled to the reaction operation. The flashed crude product is then further fractionated by passing through the first azeotropic distillation column supra.

One or more side streams, withdrawn from the stripping section of the first azeotropic distillation operation contain 97.3–451 parts, say 322 parts of methanol and 9.6–45 parts, say 32.0 parts of t-butanol. These may be returned to the reaction operation.

To the overhead stream withdrawn from the first azeotropic distillation operation, there is preferably added 6.6–31 parts, say 22 parts of a recovered recycle stream from the overhead of the second azeotropic distillation operation; and the mixture, in total amount of 144.6–673 parts, say 481 parts is admitted to a water-wash operation. Water-washing is effected at 28° C–35° C, say 32° C by admission to the operation of 26–124 parts, say 89 parts of aqueous medium, preferably substantially pure water. The weight ratio of water to charge azeotrope is 0.18–0.20, say 0.187. However, water-to-methanol ratio (in azeotrope) is 1.0–1.5, say 1.3. On a volumetric basis, the amount of water in the azeotrope may be approximately equal to the amount of methanol in the azeotrope.

During water-washing, there is formed 117.7–546 parts, say 391 parts of raffinate containing 95w%–100w%, say 98.5w% methyl t-butyl ether and 1w%–3w% say 1.5w% water. After passing through a bed of adsorbent-drier, such as a zeolite molecular sieve, the water content of the withdrawn raffinate is reduced to less than about 0.1w%. The so-dried ether is then further purified by heating to 94° C–159° C, say 120° C at 30–35 psig, say 32 psig and distilling in an ether purification operation. Bottoms may be 1.2–5.4 parts, say 4 parts of impurities including polymers. Overhead, recovered at 82° C–104° C, say 94° C, includes 115–532.6 parts, say 381 parts of desired product methyl tertiary-butyl ether.

The bottoms from the water-wash operation include the extract stream in amount of 53.1–251 parts, say 179 parts at 30° C–35° C, say 32° C and 25–40 psig, say 30 psig. This stream includes 5.6–26 parts, say 18.5 parts of methyl tertiary-butyl ether, 23–109 parts, say 77.5 parts of methanol, and 24.5–116 parts, say 83 parts of water.

The so-recovered extract stream is heated to 75° C–85° C, say 82° C at 25–40 psig, and passed to second azeotropic distillation operation. There is recovered from the stripping section thereof 21–99 parts, say 70.5 parts of methanol which is returned to the reaction operation; and, as bottoms, 24.5–116 parts, say 83 parts of water at 100° C–120° C, say 114° C. The water is recovered and may be recycled to the water-washing operation.

Overhead from the second azeotropic distillation operation, recovered at 60° C–70° C, say 66° C and 0–15 psig, say 5 psig contains 224.6–1063 parts, say 760 parts of methanol-methyl t-butyl ether azeotrope. 218–1032 parts, say 738 parts are returned as pumped reflux. Net overhead, containing 6.6–31 parts, say 22 parts of methanol-methyl t-butyl ether azeotrope is combined with the first azeotropic distillation net overhead and passed to the water-washing operation.

Bottoms from the first azeotropic distillation operation are recovered at 100° C–125° C, say 177° C and 20–35 psig, say 25 psig in amount of 46.4–219 parts, say 156 parts. They typically contain 27–129 parts, say 91 parts water, and 17.7 to 82 parts, say 59 parts t-butanol, and 1.7–8 parts, say 6 parts of methanol. In preferred operation, they are passed to the third azeotropic distillation operation. Bottoms therefrom contain 24.6–117.8 parts, say 83 parts of water. Overhead, recovered at 80° C–100° C, say 89° C and 0–15 psig, say 5 psig is recovered in amount of 114.8–559.2 parts, say 387 parts. Net overhead, containing 17.7–82 parts, say 59 parts of t-butanol and 2.4–11.2 parts, say 8 parts of water, is recycled to the reaction operation.

It is a particular feature of the process of this invention that it permits ready production and recovery of desired product ether in high purity. The process readily permits product either to be obtained which is substantially free of methanol and water. These components are undesirable because when the product ether is blended into gasoline formulations, (a) methanol will extract water from tank bottoms and (b) water will cause the gasoline to be hazy.

DESCRIPTION OF THE SPECIFIC EMBODIMENT

Practice of the process of this invention may be apparent to those skilled in the art from the following wherein, as elsewhere in this description, all parts are parts by weight unless otherwise specified. It will be apparent that the drawing is schematic and may not show details of the processing technique including e.g. pumps, vessels, heat exchangers, etc.

In the drawing, certain of the lines are identified as containing the following components:

M — methanol
E — methyl t-butyl ether
W — water
T — t-butanol
B — isobutene

It will be apparent that certain lines bearing a particular label may contain small amounts of other components.

In the drawing which represents practice of a preferred embodiment of the process of this invention, 126 parts of fresh methanol are admitted through line 10 together with 402 parts of recycle methanol admitted through line 11. To the combined mixture in line 12 there is admitted t-butanol (including fresh t-butanol from line 13 and recycle t-butanol from line 14) from line 15. As shown, lines 12 and 15 join line 16 to which is admitted through line 17 a mixture of 32 parts of t-butanol and 322 parts of methanol.

The stream in line 16 is heated in exchanger 18 to 120° C and 100 psig and (after addition of 59 parts of isobutene from line 19) is admitted through line 20 to reaction operation 21.

Charge in line 20 is admitted to etherification reaction operation 21 wherein it contacts 74 parts of Amberlyst 15 Sulfonic Acid Resin ion exchange catalyst (Rohm and Haas Inc.) at a WHSV of 21.

Amberlyst 15 is a cationic, strongly acidic, exchange resin containing a sulfonated polystyrene resin cross-linked with divinyl benzene. Reaction mixture leaves the etherification operation at 120° C and 95 psig.

Reaction mixture i.e. crude product in line 22, contains 402 parts of methanol, 91 parts of t-butanol, 59 parts of isobutene, and 385 parts of methyl t-butyl ether.

This stream is passed through line 22, cooled to 71° C in heat exchanger 23 and admitted to first azeotropic distillation operation 24 at 15 psig.

First azeotrope overhead is withdrawn from first azeotropic distillation tower 24 at 83° C through overhead line 25, condensed in condenser 26, and collected in drum 27. Isobutene in amount of 59 parts may be withdrawn through line 19 and passed to line 20. Pumped reflux may be passed through line 28; and overhead in line 29 contains 6 parts of methanol plus azeotrope including 68 parts of methanol and 385 parts of methyl t-butyl ether.

To line 29 there is added a recycle azeotrope stream in line 30 which contains 3.5 parts of methanol and 18.5 parts of methyl t-butyl ether. The combined stream in line 31 is passed to water-washed operation 32. Water (89 parts) is admitted through line 33 at 30° C and contact of water and the azeotropic mixture admitted through line 31 is effected. The weight ratio of water to azeotrope is 0.187.

Raffinate, withdrawn at 32° C through line 34, contains 381 parts of methyl t-butyl ether, 6 parts of water and 4 parts of heavier i.e. polymeric compound. Drying is effected in operation 35 wherein the liquid in line 34 contacts a bed of molecular sieves. Effluent in line 36 contains 4 parts of polymeric compounds typically di-isobutylene. The so-obtained dried ether is heated to 71° C in heat exchanger 37, and admitted to ether purification operation 38 at 10 psig.

Bottoms, recovered after reboiling in circuit 39 at 150° C include 4 parts of polymer, principally di-isobutylene and these are withdrawn through line 40. Overhead, recovered at 94° C in line 41 is condensed in condenser 42 and collected in drum 43. 590 parts of product are passed through line 44 as pumped reflux and there are recovered through line 45, 381 parts of desired product methyl t-butyl ether containing 0 parts of water.

The bottoms from water-washing operation 32 include the extract stream in total amount of 179 parts recovered in line 46 at 32° C. This extract stream includes 18.5 parts of methyl t-butyl ether, 83 parts of water, and 77.5 parts of methanol. The extract stream is heated in exchanger 47 to 82° C, and passed to second azeotropic distillation operation 48. A side stream, containing 70.5 parts of methanol and 0 parts of water are recovered at 75° C from the stripping section and passed through line 11 to line 10. After reboiling in circuit 49, 83 parts of water are recovered as net bottoms at 114° C in line 50.

Overhead from second azeotropic distillation operation 48 is recovered in amount of 760 parts at 66° C in line 51. This azeotrope, containing 15w% of methanol and 85w% of methyl t-butyl ether, is condensed in exchanger 52 and collected in vessel 53. 738 parts of pumped reflux is passed through line 54; and 22 parts of net product are withdrawn through line 30. Net product is passed as a recycle stream which joins the stream in line 29 passing, through line 31, to water-washing operation 32.

Bottoms from the first azeotropic distillation operation, after reboiling in circuit 56 are withdrawn at 117° C in amount of 156 parts through line 55. This stream, containing 91 parts of water and 59 parts of t-butanol and 6 parts of methanol is passed to third azeotropic distillation operation 57. Bottoms therefrom, after reboiling in circuit 58, include 83 parts of water recovered at 112° C in line 59.

Overhead from third azeotropic distillation opration in amount of 387 parts recovered in line 60 at 89° C is condensed in exchanger 61 and collected in vessel 62. Pumped reflux, in amount of 314 parts is passed through line 63. Net overhead in line 14 including 59 parts of t-butanol, 8 parts of water and 6 parts of methanol. This is recycled through line 14 to charge line 15 and thence to the reaction operation 21.

Although this invention has been illustrated by reference to specific embodiments, it will be apparent to those skilled in the art that various changes and modification may be made which clearly fall within the scope of this invention.

What is claimed is:

1. The process for recovering methyl t-butyl ether from a reaction effluent containing methyl t-butyl ether, methanol, t-butanol, and water which comprises:
   (a) distilling said reaction effluent in a first azeotropic distillation operation thereby forming an overhead stream containing an azeotrope of methanol and methyl t-butyl ether;
   (b) water-washing said azeotrope in a waterwashing operation thereby forming (i) a raffinate containing methyl t-butyl ether and (ii) an extract containing water, methanol, and methyl t-butyl ether;
   (c) recovering said raffinate containing methyl t-butyl ether;
   (d) distilling said extract in a second azeotropic distillation operation thereby forming (i) an overhead stream containing methanol and methyl t-butyl ether and (ii) a bottoms stream containing water;
   (e) passing said overhead stream from said second azeotropic distillation operation to said water-washing operation.

2. The process for recovering methyl t-butyl ether is claimed in claim 1 wherein said first azeotropic distillation operation is carried out at pressure of 0–30 psig.

3. The process for recovering methyl t-butyl ether as claimed in claim 1 wherein said azeotrope overhead form said first azeotropic distillation contains 13–17 w% methanol and 83–87w% methyl t-butyl ether.

4. The process for recovering methyl t-butyl ether as claimed in claim 1 wherein said raffinate from said water-washing operation is substantially free of methanol.

5. The process for recovering methyl t-butyl ether as claimed in claim 1 wherein said azeotrope overhead from said second azeotopic distillation operation has substantially the same composition as said azeotrope overhead from said first azeotropic distillation operation.

6. The process for recovering methyl t-butyl ether as claimed in claim 1 wherein said azeotrope overhead streams from said first and second azeotropic distillation operations contain about 15 w% methanol and about 85w% methyl t-butyl ether.

7. The process for recovering methyl t-butyl ether as claimed in claim 1 wherein a methanol side stream is withdrawn from each of said first and said second azeotropic distillation operations.

8. The process for recovering methyl t-butyl ether from a reaction effluent containing methyl t-butyl ether, methanol, t-butanol, and water which comprises:
   (a) distilling said reaction effluent in a first azeotropic distillation operation thereby forming an overhead stream containing an azeotrope of methanol and methyl t-butyl ether;
   (b) water-washing said azeotrope in a water-washing operation at a water-to-charge azeotrope weight ratio of about 0.18–0.20, thereby forming (i) a raffinate containing methyl t-butyl ether and (ii) an extract containing water, methanol, and methyl t-butyl ether;

(c) recovering said raffinate containing methyl t-butyl ether;

(d) distilling said extract in a second azeotropic distillation operation thereby forming (i) an overhead stream containing methanol and methyl t-butyl ether and (ii) a bottoms stream containing water; and (e) passing said overhead stream from said second azeotropic distillation operation to said water-washing operation.

9. The process for recovering methyl, t-butyl ether from a reaction effluent containing methyl t-butyl ether, methanol, t-butanol, and water which comprises:

(a) distilling said reaction effluent in a first azeotropic distillation operation thereby forming an overhead stream containing an azeotrope of methanol and methyl t-butyl ether;

(b) water-washing said azeotrope in a water-washing operation thereby forming (i) a raffinate containing methyl t-butyl ether and (ii) an extract containing water, methanol, and methyl t-butyl ether;

(c) recovering said raffinate containing methyl t-butyl ether;

(d) distilling said extract in a second azeotropic distillation operation thereby forming (i) an overhead stream containing methanol and methyl t-butyl ether and (ii) a bottoms stream containing water;

(e) passing said overhead stream from said second azeotropic distillation operation to said water-washing operation;

(f) withdrawing from said first azeotropic distillation operation a bottoms stream containing t-butanol and water;

(g) distilling said bottoms stream from said first azeotropic distillation operation in a third azeotropic distillation operation thereby forming an overhead containing t-butanol; and (h) recovering said overhead containing t-butanol.

* * * * *